(12) United States Patent
Kjaer et al.

(10) Patent No.: US 11,629,368 B2
(45) Date of Patent: Apr. 18, 2023

(54) OUTER LAYER FOR ENZYME SENSORS

(71) Applicant: Radiometer Medical ApS, Brønshøj (DK)

(72) Inventors: Thomas Kjaer, Smoerum (DK); Thomas Steen Hansen, Herlev (DK); Lydia Dahl Clausen, Lynge (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 522 days.

(21) Appl. No.: 15/776,252

(22) PCT Filed: Nov. 23, 2016

(86) PCT No.: PCT/EP2016/078529
§ 371 (c)(1),
(2) Date: May 15, 2018

(87) PCT Pub. No.: WO2017/089380
PCT Pub. Date: Jun. 1, 2017

(65) Prior Publication Data
US 2020/0248224 A1 Aug. 6, 2020

(30) Foreign Application Priority Data
Nov. 27, 2015 (DK) .......................... PA 2015 00755

(51) Int. Cl.
*C12Q 1/00* (2006.01)
*C08L 33/12* (2006.01)
(Continued)

(52) U.S. Cl.
CPC .............. *C12Q 1/002* (2013.01); *C08L 33/12* (2013.01); *G01N 27/3271* (2013.01);
(Continued)

(58) Field of Classification Search
CPC ........................... C12Q 1/002; G01N 27/3271
See application file for complete search history.

(56) References Cited

U.S. PATENT DOCUMENTS 5,696,314 A * 12/1997 McCaffrey ............. C12Q 1/002
435/14
5,707,502 A * 1/1998 McCaffrey ............. C12Q 1/001
204/403.1
(Continued)

FOREIGN PATENT DOCUMENTS

CN   101128599 A   2/2008
CN   201398971 Y   2/2010
(Continued)

OTHER PUBLICATIONS

Wikipedia: creatiniase (Year: 2020).*
(Continued)

*Primary Examiner* — Luan V Van
*Assistant Examiner* — Caitlyn Mingyun Sun
(74) *Attorney, Agent, or Firm* — Finnegan, Henderson, Farabow, Garrett & Dunner, LLP (57) ABSTRACT

The present application discloses a planar enzyme sensor for measuring the concentration of an analyte in a solution comprising a substrate of an electrically insulating material supporting an electrode layer of an electrically conductive material. The substrate and electrode layer have a plurality of layers disposed thereon which include an enzyme layer and a microporous outer layer covering the enzyme layer, wherein the outer layer comprises a continuous phase of a water-resistant polymer (e.g. a polyvinylacetate or an acrylate copolymer), a protein, a enzyme (e.g. an enzyme) embedded in the continuous phase, and possibly polytetrafluoroethylene particles. The enzyme and the polytetrafluoroethylene particles provide a controlled porosity to the outer membrane.

13 Claims, 1 Drawing Sheet

(51) Int. Cl.
*G01N 27/327* (2006.01)
*G01N 27/40* (2006.01)
(52) U.S. Cl.
CPC .......... *G01N 27/40* (2013.01); *C08L 2203/20* (2013.01); *C08L 2205/03* (2013.01); *C08L 2207/02* (2013.01)

(56) References Cited

U.S. PATENT DOCUMENTS

| | | | | |
|---|---|---|---|---|
| 7,959,791 | B2* | 6/2011 | Kjaer | C12Q 1/002 204/403.06 |
| 8,080,385 | B2* | 12/2011 | Heller | C12Q 1/006 435/14 |
| 2003/0217966 | A1* | 11/2003 | Tapsak | A61B 5/1486 210/500.21 |
| 2007/0135698 | A1* | 6/2007 | Shah | C12Q 1/006 204/520 |
| 2010/0116691 | A1 | 5/2010 | Papadimitrakopoulos et al. | |

FOREIGN PATENT DOCUMENTS

| | | |
|---|---|---|
| CN | 102326072 A | 1/2012 |
| EP | 1 502 957 A1 | 2/2005 |
| EP | 1 885 871 B1 | 2/2008 |
| JP | 57-74653 | 5/1982 |
| JP | S60173452 A | 9/1985 |
| JP | H0862173 A | 3/1996 |
| JP | 2001-506742 | 5/2001 |
| JP | 2005-531755 | 10/2005 |
| JP | 2008-502921 | 1/2008 |
| JP | 2008-256725 | 10/2008 |
| JP | 2009-500083 A | 1/2009 |
| JP | 2009-519106 | 5/2009 |
| JP | 2012-513821 A | 6/2012 |
| WO | WO 02/097414 A2 | 12/2002 |
| WO | WO 03/100083 A1 | 12/2003 |
| WO | WO 2005/123938 A1 | 12/2005 |
| WO | WO 2006/122554 A2 | 11/2006 |
| WO | WO 2007/005759 | 1/2007 |
| WO | WO 2007/070486 A2 | 6/2007 |
| WO | WO 2010/075029 | 7/2010 |

OTHER PUBLICATIONS

99 Creatinase-from-E-coli,-Recombinant. (Year: 2020).*
N. Saba, Chapter 6, Thermal properties of oil palm biomass based composites, Lignocellulosic Fibre and Biomass-Based Composite Materials, 2017, Elsevier Ltd.; pp. 95-122. (Year: 2017).*
International Search Report for International Application No. PCT/EP2016/078529, dated Jan. 30, 2017.
Written Opinion of the International Searching Authority for International Application No. PCT/EP2016/078529.
Braha, Orit et al., "Designed protein pores as components for biosensors," Chemistry & Biology, vol. 4, No. 7, pp. 497-505 (1997).

* cited by examiner

OUTER LAYER FOR ENZYME SENSORS

This application is a national stage filing under 35 U.S.C. § 371 of International Application No. PCT/EP2016/078529, filed on Nov. 23, 2016, which claims priority of Danish Patent Application No. PA 2015 00755, filed Nov. 27, 2015. The contents of these applications are each incorporated herein by reference.

FIELD OF THE INVENTION

The present invention relates to planar enzyme sensors for measuring the concentration of an analyte in a solution.

BACKGROUND OF THE INVENTION

Analyte sensors such as biosensors include devices that use biological elements to convert a chemical analyte in a matrix into a detectable signal. There are many types of biosensors used to detect wide variety of analytes. Among the various types of biosensors, electrochemical biosensors are typically based on enzyme-catalysed oxidation of the analyte. The enzyme is interposed and immobilised between two membranes, the first or outer of which comes in contact with the sample to be assayed and permits access of analyte and of oxygen to the enzyme from the sample while restricting the passage of proteins, red blood cells, and other macromolecules, and the second which is in close relationship with the face of the sensor electrode and permits access of hydrogen peroxide to the electrode while at the same time excluding passage of interfering substances having a molecular weight greater than about 250 g/mol, e.g., ascorbic acid, acetaminophen, and salicylic acid. In practice the sample to be assayed, which contains both analyte and oxygen, is brought in contact with the outer face of the first or outer membrane. Diffusion of the sample through the membrane into contact with the immobilized enzyme leads to an oxygen consuming reaction, and diffusion of the resulting hydrogen peroxide through the second or inner membrane into contact with the sensor electrode causes development of an electrical current which can then be read by conventional means. However, analyte assays conducted as in the prior art have lacked accuracy in the case of solutions having high concentration of analytes, as are often found for example in undiluted whole blood or serum, or when the enzymes available for the sensors have intrinsically low conversion rates or are readily affected by inhibitors in the sample, or for samples having a low oxygen concentration. In order to obtain consistent and accurate measurements, particularly when the samples to be assayed have a high concentration of analytes, the outer membrane must have a high degree of homogeneity with respect to thickness, pore size and pore distribution.

U.S. Pat. No. 5,696,314 discloses an enzyme sensor comprising an immobilized enzyme layer and a microporous layer. The microporous layer is designed to limit the rate at which the analyte reaches the immobilized enzyme layer while providing good oxygen transport so that oxygen does not function as the rate limiting reagent in the reaction which occurs in the enzyme layer. The microporous layer includes a polymer powder, a mineral powder, a polymer binder and at least one surfactant.

US 2005/0009130 A1 discloses a castable diffusion membrane for enzyme-based sensors. The membrane comprises a polymer material and pore-forming particles dispersed in the polymer material. The polymer material is typically selected from non-water soluble polymer like polyurethane, polyacrylamide, polystyrene, polyvinylesters and copolymers of e.g. butadiene and styrene. The pore-forming particles are typically stable particles which possess an inherent and defined porosity, e.g. inorganic and organic particles like Kieselguhr, silica gel, cellulose, precipitated gypsum, kaolin, glass, diatomeous earth and the like.

DE 10 2004 003 793 A1 discloses an electrochemical biosensor with improved storage stability. It comprises a two-layer membrane of a first layer of an aqueous polymer-dispersion (such as of polyvinylacetate, acrylate copolymers (e.g. copolymers of ethylacetate and methylmethacrylate)) having e.g. an enzyme embedded therein, and a second (outer) layer of a thin water-resistant, permeable cover layer.

EP 1 282 417 B1 discloses a method for producing a biosensor (in particular a creatinine sensor) in which method a first enzyme in combination with a surface-active substance is applied to a working electrode in a first step, and a second enzyme is chemically immobilized thereupon in a subsequent step.

The membranes of the prior art have generally been so highly permeable to the passage of analyte or had inhomogeneous distribution of permeable porosity that, particularly in the case of samples having high concentrations of analyte, low concentrations of oxygen or when the enzymes available for the sensors have intrinsically low conversion rates, the amount of analyte coming in contact with the immobilized enzyme either overall or locally exceeds the amount of oxygen available. Consequently, the oxygen concentration is the rate limiting component of the reaction rather than the analyte concentration, so that the accuracy of the analyte assay is destroyed.

BRIEF DESCRIPTION OF THE INVENTION

The present inventors have surprisingly found that enzymes and other proteins as pore forming agents in aqueous polymer dispersions provides outer membranes with high reproducibility with respect to analyte permeability, porosity homogeneity, thickness and in-use stability.

One aspect of the invention relates to a planar enzyme sensor, cf. claim 1.

Another aspect of the invention relates to a method for the preparation of the enzyme sensor, cf. claim 11.

DETAILED DISCLOSURE OF THE INVENTION

The present invention relates to the field of planar enzyme sensors for determining various analytes in solutions, such as samples of biological origin. Typical analytes are cholesterol, sucrose, glutamate, ethanol, ascorbic acid, fructose, pyruvate, ammonium, nitrite, nitrate, phenol, NADH, glucose, lactate, creatine, creatinine, Human Serum Albumin, IgG and haemoglobin (e.g. glycated haemoglobin, HbA1c).

The term "planar" should be understood in contrast to traditional rod like electrodes. The planar enzyme sensors described herein are typically applicable as multiple-use enzyme sensors. When used herein, the term "multiple-use" is intended to mean a sensor, which after analyte measurement is regenerated by means of rinsing with buffer, thus restoring the current to the base line value and readying the sensor for assay of a new sample array.

When used herein, the term "sample of biological origin" is intended to mean liquid samples taken from physiological fluids. Illustrative examples hereof are those like blood (e.g. whole blood, blood plasma, blood serum, blood fractions, etc.), urine, dialysate and pleura.

Enzyme Sensors

As mentioned above, the present invention i.a. provides a planar enzyme sensor for measuring the concentration of an analyte in a solution, such as a sample of biological origin. The sensor comprises a substrate of an electrically insulating material supporting an electrode layer of an electrically conductive material, wherein the substrate and electrode layer have a plurality of layers disposed thereon, and wherein the plurality of layers at least include: (a) an enzyme layer; and (b) a microporous outer layer covering the enzyme layer. The outer layer comprises (i) a continuous phase of a water-resistant polymer and (ii) a protein embedded in said continuous phase. The outer layer may further comprise (iii) polymer particles.

Generally, enzyme sensors are characterized by having an enzyme layer capable of converting the analyte into a species which is detectable at the electrode.

The enzyme sensors described herein can be adapted for a wide variety of analytes, in particular enzyme substrates and/or co-substrates. Examples of such enzyme substrates are cholesterol, sucrose, glutamate, ethanol, ascorbic acid, fructose, pyruvate, ammonium, nitrite, nitrate, phenol, NADH, glucose, lactate, HbA1c, creatine and creatinine. Of particular interest are glucose, lactate, ethanol, creatine, and creatinine. Hence, examples of enzyme sensors are creatinine sensors (i.e. a dual sensor set-up consisting of a creatinine sensor and creatine sensor), glucose sensors, lactate sensors, etc.

Substrate and Electrode

The substrate and the electrode can be provided according to conventional method, e.g. as disclosed in U.S. Pat. No. 7,195,697 and as described in Example 1 for the creatinine sensor.

Typical substrates are those of aluminium oxide, glass, silica, printed circuit boards, plastic films and paper, and typical electrodes are prepared from polymers, glasses and metals like gold, platinum, palladium, silver(chloride) and carbon.

Interference Removal Layer

The electrode may optionally be covered with an interference removal layer (i.e. a layer between the electrode and the enzyme layer), which function is to prevent possible electrochemical interferences in blood from being oxidized at the electrode. The layer should allow for the passage of hydrogen peroxide but not for larger molecules. Possible interferences could be e.g. ascorbic acid or paracetamol. Examples of possible interference removing layers are cellulose acetate, cellulose acetate butyrate and poly(o-phenylenediamine).

The Enzyme Layer

The enzyme layer comprises at least one enzyme. The enzyme layer can for example comprise oxidative enzymes such as glucose oxidase, lactate oxidase, sarcosine oxidase or cholesterol oxidase. The enzyme layer may also comprise an enzyme mixture such as, for example, an enzyme cascade, which makes possible the detection of analytes which cannot be directly detected such as, for example, creatinine. Creatinine cannot be enzymatically oxidized by a simple enzyme but requires several enzymatic steps to generate an analyte derivative which is detectable by amperometric means. A suitable enzyme cascade system for the detection and/or determination of creatinine can comprise, e.g., creatinine aminohydrolase (in short "creatininase" or "CA"), creatine amidinohydrolase (in short "creatinase" or "CI"), and sarcosine oxidase (in short "SO").

In some embodiments, the enzyme layer comprises a polymer matrix in which the at least one enzyme is embedded.

It should be understood that the enzyme(s) of the enzyme layer alone must be capable of converting the analyte into a detectable species. Hence, even if the outer layer includes an enzyme which can convert the analyte, the enzyme layer should not be absent of this enzyme because the conversion to detectable species should take place as near as possible to the electrode in order to provide high sensitivity and linearity.

The Outer Layer

The outer layer (a diffusion membrane) for the planar enzyme sensor is much different from e.g. the track etched diffusion limiting membrane on a conventional enzyme sensor in respect to porosity, morphology and diffusion mechanism through the layer/membrane. In track-etched membranes, the pore size is much larger than the analyte sizes. Here the diffusion coefficients of analytes and relevant substances, like e.g. glucose, lactate, creatinine, and $H_2O_2$, are approximately similar to the diffusion coefficient in pure aqueous media.

The outer layer of the planar enzyme sensor described herein is assumed to consist of much smaller and uniformly distributed pores in which all transport of water and substances (including analytes) takes place. As the pores are assumed to be twisted, the outer layer has a tortuosity, i.e. the effective pore length is larger than the thickness of the layer. Because the pore size is in the same range as the diffusing substances, friction partly occurs between the substance and the pore wall. Especially pore sizes in the range between the size of the analyte (e.g. creatinine) and $H_2O_2$ is problematic because $H_2O_2$ in such a situation will have a fast diffusion in and through the outer layer whereas the analyte (e.g. creatinine) will be hindered. The diffusion of the analyte (e.g. creatinine) into the enzyme layer will then be limited, resulting in a decrease in formation of the detection target, $H_2O_2$, which has a relatively larger diffusion constant out of the outer layer, and this reduces the sensor sensitivity severely. The optimal situation is where the diffusion coefficients ratio for the analyte (e.g. creatinine) over $H_2O_2$ is comparable to the aqueous diffusion coefficient ratios. This requires a minimum distance between polymer chains in the swelled porous phase well above the molecular size of e.g. creatinine (7-9 Å).

In order for the diffusion of analytes to be unhindered, the pore diameter must be significantly larger than the diameter of the analyte. Hence the friction between the analyte molecules and the pore wall must not be too large compared to the friction between $H_2O_2$ and the pore wall, because this favors the diffusion of $H_2O_2$ over the analyte (e.g. creatinine) in the porous phase and thereby reduces sensitivity.

The outer layer of the enzyme sensor thus provides the sensor with a controlled permeability. Especially in connection with sensors which use oxygen consumption as a means for analyte determination, the outer layer shows significant advantages. The pores created by the proteins, which function as pore-forming particles, allow for the adjustment of diffusion of the analyte molecules, e.g. creatinine, glucose, etc., across the outer layer, and the choice of the water-resistant polymer (and the optional polymer particles) influences the permeability of oxygen. Although oxygen permeation across the outer layer in part is also possible through the pores created by the polymer particles (if present), it is essentially influenced by the water-resistant polymer, especially if this has a high oxygen permeability.

Hence, interesting advantages are provided by the microporous outer layer of the present enzyme sensor. The outer layer comprises (i) a continuous phase of a water-resistant polymer, (ii) a protein embedded in said continuous phase and optionally (iii) polymer particles, as will be described in further details below.

(i) The Water-Resistant Polymer

The water-resistant polymer provides a continuous phase wherein (ii) one or more proteins (e.g. an enzyme) and possibly also (iii) polymer particles are embedded. This continuous phase at the same time functions as a binder towards the underlying enzyme layer and provides structural integrity to the outer layer. A typical low glass-transition temperature ($T_g$) of the polymer enables it to expand/contract as components are being hydrated or washed out of the sensor.

When used herein, the term "water-resistant" is intended to mean that it is nearly unaffected when exposed to water, thus the water absorption is so low that the bulk polymer remains impermeable to analytes and detecting species, e.g. hydrogen peroxide.

Typically, the glass-transition temperature ($T_g$) of the water-resistant polymer is below 100° C., such as in the range of 0-60° C., e.g. 5-60° C.

Illustrative examples of suitable water-resistant polymer types for the purpose of the outer layer are those selected from polyvinylacetates and its copolymers, acrylate or methacrylate copolymers, polyurethanes and silicones, in particular from polyvinylacetates and copolymers of ethylacrylate and methylmethacrylate.

Among the polyvinylacetates can e.g. be mentioned polyvinylacetate. Such polymers are commercially available under the tradename Kollicoat, e.g. Kollicoat SR, wherein polyvinylacetate stabilized with polyvinylpyrrolidone (PVP). The stabilizer polyvinylpyrrolidone also acts as a poreforming ingredient, however less efficient than (ii) the one or more proteins.

Among the acrylate copolymers can e.g. be mentioned copolymers of ethylacrylate and methylmethacrylate, such as those having 20-99% (w/w) of methylmethacrylate monomers. Such polymers are commercially available under the tradename Eudragit, e.g. Eudragit NM (such as Eudragit NM30D), Eudragit RS, and Eudragit E100.

Currently preferred examples of commercially available water-resistant polymers are Eudragit NM30D and Kollicoat SR30D.

Copolymers of ethylacrylate and methylmethacrylate like those available under the tradename Eudragit are available in the form of water-based latexes, thus the solvent is as gentle as possible to the sensitive enzymes of the enzyme layer.

One of the more interesting aqueous polymer dispersions, due to the low glass transition temperature, is Eudragit NM30D supplied by Evonik Industries as a milky-white aqueous dispersion of low viscosity having a pH of 5.5-8.6. It contains approximately 30% (approximately 28.5-31.5%) w/w particles of the copolymer poly(ethylacrylate-co-methylmethacrylate) and approximately 0.7% w/w Macrogol stearyl ether as emulsifier. Eudragit NM has low film forming temperature (5° C.), low permeability, pH independent swelling, is highly flexible and has weight average molar mass of 600,000 g/mol. It is therefore soft and slightly sticky at room temperature as well as at 37° C. It acts as a continuous binding phase in the membrane system and improves the integrity and the cohesion of the membrane. The hydrodynamic size of the concentrated and diluted Eudragit NM30D particles was measured to be approximately 0.175 µm. In order to produce a membrane with enhanced analyte permeability, Eudragit NM30D is mixed with a component having a higher solubility in water than said poly(ethylacrylate-co-methylmethacrylate), i.e. a protein like creatinase.

Preferably, the water-resistant polymer constitutes 15-80%, such as 20-60%, in particular 20-30%, based on the total volume of the outer layer.

(ii) The One or More Proteins

A special feature of the outer layer is the use of (ii) one or more proteins, which are considered as semi-hard particles, as pore-formers. Surprisingly it has been found, that the use of the same enzymes, as are used in the enzyme layer, is an efficient way to stabilize the sensitivity as a function of time. The benefit of using the same enzymes as present in the enzyme layer of the sensor as pore-formers in the outer layer is believed to be that it reduces lack of enzyme activity over the in-use lifetime of the sensor. Surprisingly creatinase was found to be a well behaved pore-former additive for a creatinine sensor, which also renders the outer layer more reproducible, more homogenous with regard to porosity and of more constant sensitivity over time.

The role of the protein(s) (such as enzymes) as pore-former is not fully understood, but one role is the positive effect of raising the creatinase surplus in the sensor and thereby its in-use lifetime, another role is providing the outer layer with optimal diffusion properties of analytes and co-analytes as e.g. $H_2O_2$. This is primarily by the enzymes three-dimensional structure and its water uptake capacity, as the enzyme activity in the outer layer does not appear to be necessary for the sensor function during the whole lifetime of the sensor. Leaching studies have shown that a large fraction of the creatinase initially present in the outer layer leaches out during the first 24 h of in-use, and that more than 80% is leaching out already within the first hours. This is a surprising result as the leaching of most other hydrophilic pore-formers has caused decreasing sensitivity over time, which normally is interpreted as decreasing porosity of the outer layer caused by the loss of the pore-former. However when the water soluble enzyme creatinase, initially present in the outer layer, leaches out, the porous structure is maintained and becomes filled with water and salts which keep the pores open and stabilizes the permeability to the outer layer.

The embedded protein(s) are believed to provide a continuous, water-filled porosity throughout the outer layer. For example, when a creatinase enzyme is included in the outer layer, the porosity and sensor sensitivity is proportional to the enzyme concentration of the outer layer. Conveniently, the creatinase enzyme is the one enzyme lacking the most in the enzyme layer because of poor activity and stability. The homogenous porosity throughout the entire area and thickness of the outer layer provides a homogeneous diffusion of analyte to all enzyme molecules in the enzyme layer, thus the sensors appears to have more enzyme surplus and longer in-use stability.

Suitable proteins are those which have a globular structure in aqueous solutions. Typically, the molecular weight of the proteins is in the range of 30,000-400,000 g/mol, such as 100,000-200,000 g/mol. In some embodiments, the protein is cross-linked so as to at least double the (average) molecular weight.

In an interesting embodiment, the protein embedded in the continuous phase is an enzyme. Examples of suitable proteins or enzymes are those selected from albumin, creatinase and other hydrolases, in particular creatinase.

In a currently preferred embodiment, the pore-forming enzyme is creatinase. The enzyme creatinase (CI) is water soluble, existing in solution as a dimer, with a molecular weight of 47,000 g/mol and forms an approximately globular three-dimensional structure in aqueous solutions with both hydrophilic and hydrophobic moieties and ionic groups. Their iso-electrical points are around 5.4 so they will have a net negative charge at pH 7.4. The semi-hard particles of the enzyme mean that at room temperature the helical and beta sheet conformation of the enzyme is not destroyed and enzyme crystals morphology in solution is retained. The hydrodynamic size of the concentrated and diluted uncrosslinked creatinase enzyme was measured to be 3-5 nm with small impurities and 1-3 nm with perhaps some aggregated enzyme respectively. The creatinase enzyme used as pore-former is cross-linked to approximately double molecular size, approximately 6-10 nm in diameter.

Preferably, the one or more proteins, such as one or more enzymes, constitutes 1-30%, such as 4-25%, in particular 7-15%, based on the total volume of the outer layer.

(iii) The Polymer Particles

The microporous outer layer may further comprise (iii) polymer particles embedded in said continuous phase. The polymer particles are typically water-resistant polymer particles which have low water absorption and are so abundant that they end up constituting a structure that resembles a rhombohedral crystalline-like mesh inside the outer layer. These features improve the sensor sensitivity, enzyme surplus and linearity. Moreover, the high oxygen solubility of the polymer particles, e.g. PTFE particles, reduces the oxygen dependence and increases the linearity further.

The polymer particles used as a rhombohedral crystalline-like mesh are typically stable synthetic polymer particles that do not aggregate nor repel each other significantly in aqueous media. It should be understood with respect to the (ii) proteins also present in the outer layer that the polymer particles are not of protein origin.

The size of the particles constituting the rhombohedral crystalline-like mesh is typically between about 2 and 500 nm and, more typically from about 50 to 200 nm.

It has been found that adding a relatively large volume fraction of polymer particles, like hard PTFE particles, to the aqueous dispersion has a positive effect on the homogeneity and reproducibility of the outer layer. Thereto the analyte permeability of the outer layer becomes less sensitivity to variations in thickness of the outer layer. The reason for this is believed to be because the diffusion in highly filled composite systems takes place in the large interface between the hard filler particles and the polymer binder phase, so there is a high degree of interconnectivity which essentially has the same geometry all over in the outer membrane layer.

The high amount of polymer particles is expected to make the morphology of the outer layer less sensitive to smaller variations in thickness, compared to if the interconnectivity was established by a smaller content or more coarse particles, and this should give a more reproducible outer layer with respect to membrane permeability.

If present, the outer layer typically comprises hard polymer particles in an amount of from 0.5 to 80%, more typically from 30 to 70%, more typical from 40 to 60%, based on the total volume of the outer layer.

In contrast to the water-resistant polymer, the polymer particles are very hydrophobic and have no water absorption or at the most 1% water absorption. The polymer particles have no function as a binder and can therefore have a higher glass-transition temperature ($T_g$) than the water-resistant polymer, which act as binder phase upon drying of the layer.

For the use as rhombohedral crystalline-like mesh forming polymer particles in the outer layer, essentially all stable particles and mixtures of such particles are in principle useful, which particles possess an inherent and defined porosity. According to the desired application, suitable rhombohedral crystalline-like mesh forming polymer particles are believed to include natural or synthetic polymers, which in aqueous solution have a three-dimensional structure. In contrast to the "soft" pore-forming proteins, which adds porosity to the outer layer by leaving a porous volume after water-absorption (and after possible wash out of the protein), the "hard" rhombohedral crystalline-like mesh forming polymer particles, are believed to add porosity to the system by its surface area, where the diffusion and the pore-forming proteins takes place along the interface between the hard particles and the binder of the water-resistant polymer (dispersion particles).

The hard polymer particles are added in order to obtain an even more homogeneously and well dispersed porous phase, e.g. as the case may be for a Eudragit/PTFE hydrophobic polymer matrix. In this case, the outer layer has low water absorption due to the PTFE, which improves the sensor sensitivity and linearity and the high oxygen solubility of PTFE reduces oxygen dependence.

In one interesting embodiment, the polymer particles are selected from fluorocarbon polymers including particles from polytetrafluoroethylene (PTFE), polytrifluoroethylene, polyvinylfluoride, polyvinylidenefluoride, polychlorotrifluoroethylene, polyfluoroethylenepropylene, polyperfluoroalkoxyethylene and copolymers thereof. For simplicity of description, the specification will refer to the preferred fluorocarbon polymer, polytetrafluoroethylene (PTFE).

Polytetrafluoroethylene (PTFE) is a synthetic fluoropolymer originally made by DuPont. PTFE generally has a high density (around 2.2 g/cm$^3$) and high melting point (approximately 327° C.). The high density together with high melting point makes these particles hard. At atmospheric pressures, crystalline or partially crystalline polytetrafluoroethylene (usually the degree of crystallinity is 90 to 95%) undergoes several phase changes from sub-ambient temperatures up to the melting point. Below 19° C., a well-ordered hexagonal crystal structure by crowding of the fluorine atoms around the main carbon chain is obtained, which forces a helical conformation of the polymer backbone in the crystal lattice. PTFE does undergo a phase change at 190° C. and will increase in volume by 1.2%. Polytetrafluoroethylene (PTFE) polymer with the commercial name of "Teflon® PTFE 60% (w/w) aqueous dispersion" having basic pH 10-11 is supplied by Sigma Aldrich.

The PTFE dispersion comprises approximately 6% (w/w) non-ionic surfactant, ethoxylated trimethylnonyl ether (Tergitol TMN-10 type, Mw 230 g/mol). The hydrodynamic size of the concentrated and diluted PTFE particles was measured to be 0.9 µm and 0.3 µm respectively.

Embodiments

In one embodiment, the outer layer of the planar enzyme sensor (in particular a creatine or creatinine sensor) comprises a water-resistant polymer selected from copolymers of ethylacrylate and methylmethacrylate (e.g. Eudragit NM30D) in an amount of 20-30%, an enzyme (in particular creatinase) in an amount of 10-20% and polymer particles in an amount of 50-60%, based on the total volume of the outer layer.

In another embodiment, the outer layer of the planar enzyme sensor (in particular a creatine or creatinine sensor) comprises a water-resistant polymer selected from copolymers of ethylacrylate and methylmethacrylate (e.g. Eudragit NM30D) in an amount of 70-80% and an enzyme (in particular creatinase) in an amount of 20-30%, based on the total volume of the outer layer.

In yet another embodiment, the outer layer of the planar enzyme sensor (in particular a creatine or creatinine sensor) comprises a water-resistant polymer selected from polyvinylacetate (e.g. Kollicoat SR30D) in an amount of 20-30%, an enzyme (in particular creatinase) in an amount of 10-20% and polymer particles in an amount of 50-60%, based on the total volume of the outer layer.

In still another embodiment, the outer layer of the planar enzyme sensor (in particular a creatine or creatinine sensor) comprises a water-resistant polymer selected from polyvinylacetate (e.g. Kollicoat SR30D) in an amount of 70-80% and an enzyme (in particular creatinase) in an amount of 20-30%, based on the total volume of the outer layer.

The relative volume ratio between the water-resistant polymer and the protein, in the cases where the outer layer do not comprise hard polymer particles, is preferably 90:10 to 60:40, such as 85:15 to 60:40, or 80:20 to 75:25.

The relative volume ratio between the water-resistant polymer, the protein and the polymer particles, in the cases where the outer layer comprise polymer particles, is preferably between 40:20:40 to 50:10:40 to 20:10:70.

The outer layer may also comprise additional constituents like buffers, salt, surfactants, wetting agents, pigments like titanium dioxide (for improved remission properties of the outer layer), etc. in an amount of up to 10%, such as up to 2%, based on the total volume of the outer layer.

There are a number of interactions among different materials described above when mixed together. In the interaction of colloidal particles van der Waals forces, electrostatic interaction and steric repulsive forces can play an important role. The interacting colloidal particles can cause stability problems such as aggregation, flocculation or phase separation. The stability of particle dispersion depends upon the balance of the repulsive and attractive forces that exist between particles as they approach one another.

In composite membranes such as the present outer layer, the diffusion typically takes place along the surface of the inert filler particles. This means, that their distribution in the polymer matrix to a large extent defines the diffusion pathway through the outer layer. Because the continuous phase of Eudragit NM particles is impermeable to analytes, the diffusion of analytes will take place in the water filled and continuous phase defined by the pore making enzyme particles. Upon drying of the outer layer, the emulsifiers and enzyme molecules will tend to concentrate in the open space between the polymer particles, and their presence in the dried outer layer will cause water absorption in amounts sufficient for the analytes to diffuse.

Specific Embodiments

In one embodiment, the enzyme sensor is a creatine sensor. In this embodiment, the enzyme layer comprises sarcosine oxidase and creatinase. In some interesting variants hereof, the protein in the outer layer is an enzyme, in particular creatinase.

In one variant of the creatine sensor, the outer layer comprise a water-resistant polymer selected from copolymers of ethylacrylate and methylmethacrylate (e.g. Eudragit NM30D) in an amount of 20-30% (in particular 24-28%), an enzyme (in particular creatinase) in an amount of 7-12% (in particular 8-10%), and PTFE polymer particles in an amount of 50-65% (in particular 55-60%), based on the total volume of the outer layer.

The amount of pore-forming enzyme should be large enough to provide connecting porosity from one side of the outer layer to the other. As the percolation threshold is around 15% this is achieved with approximately 9% enzyme, which after water absorption counts for nearly 15% porosity. If the amount is too high, the sensitivity is reduced due to relatively too large back diffusion of hydrogen peroxide and the in-use stability will be reduced too because of leaking of enzyme from the enzyme layer. The amount of hard polymer particles must be above the percolation threshold in attempt to secure physical contact between the particles throughout the layer. We have found that the sensitivity and in-use stability increases with the amount of PTFE particles up to approximately 60% and best performance is with 50-60% v/v. The PTFE guides the porosity because the diffusion takes place along the particle surfaces. Thereto it is hydrophobic and reduces the water uptake of the membrane in-use, which stabilizes the permeability over time. The polymer particles in the dispersion has a relatively low film forming temperature (5° C.), which makes it possible to cure the layer at room temperature, and which is beneficial for enzymes, which do not withstand high drying temperatures.

In another embodiment, the enzyme sensor is a creatinine sensor. In this embodiment, the enzyme layer comprises sarcosine oxidase, creatinase and creatininase. In some interesting variants hereof, the protein in the outer layer is an enzyme, in particular creatinase.

In one variant of the creatinine sensor, the outer layer comprise a water-resistant polymer selected from copolymers of ethylacrylate and methylmethacrylate (e.g. Eudragit NM30D) in an amount of 20-30% (in particular 24-28%), an enzyme (in particular creatinase) in an amount of 7-12% (in particular 8-10%), and PTFE polymer particles in an amount of 50-65% (in particular 55-60%), based on the total volume of the outer layer.

The same considerations as above for the creatine sensor also apply for the creatinine sensor.

In yet another embodiment, the enzyme sensor is a glucose sensor. In this embodiment, the enzyme layer comprises glucose oxidase. In some interesting variants hereof, the protein in the outer layer is an enzyme, in particular the same creatinase enzyme. Note that in the glucose sensor the creatinase enzyme only functions as a pore-forming agent.

In particular for the glucose sensor, the outer layer comprise a water-resistant polymer selected from a water-resistant polymer selected from copolymers of ethylacrylate and methylmethacrylate (e.g. Eudragit NM30D) in an amount of 20-35%, an enzyme (in particular creatinase), in an amount of 0.5-3.0%, and PTFE polymer particles in an amount of 65-80%, based on the total volume of the outer layer.

In still another embodiment, the enzyme sensor is a lactate sensor. In this embodiment, the enzyme layer comprises lactate oxidase. In some interesting variants hereof, the protein in the outer layer is an enzyme, in particular creatinase.

In particular for the lactate sensor, the outer layer comprise a water-resistant polymer selected from a water-resistant polymer selected from copolymers of ethylacrylate and methylmethacrylate (e.g. Eudragit NM30D) in an amount of 20-35%, an enzyme (in particular creatinase) in an amount of 0.5-3.0%, and PTFE polymer particles in an amount of 65-80%, based on the total volume of the outer layer.

In still another embodiment, the enzyme sensor is an alcohol sensor. In this embodiment, the enzyme layer comprises alcohol oxidase. In some interesting variants hereof, the protein in the outer layer is an enzyme, in particular creatinase.

In particular for the alcohol sensor, the outer layer comprise a water-resistant polymer selected from a water-resistant polymer selected from copolymers of ethylacrylate and methylmethacrylate (e.g. Eudragit NM30D) in an amount of 20-35%, an enzyme (in particular creatinase) in an amount of 0.5-3.0%, and PTFE polymer particles in an amount of 65-80%, based on the total volume of the outer layer.

In still another embodiment, the enzyme sensor is a urea sensor. In this embodiment, the enzyme layer comprises urease. In some interesting variants hereof, the protein in the outer layer is an enzyme, in particular creatinase.

In particular for the urea sensor, the outer layer needs to be relatively open, therefor the outer layer comprise a water-resistant polymer selected from a water-resistant polymer selected from copolymers of ethylacrylate and methylmethacrylate (e.g. Eudragit NM30D) in an amount of 20-35%, an enzyme (in particular creatinase) in an amount of 5-15%, and PTFE polymer particles in an amount of 50-75%, based on the total volume of the outer layer.

Method for the Preparation of the Planar Enzyme Sensor

The invention further provides a method for the preparation of the planar enzyme sensor described hereinabove, said method comprising the steps of:

a. providing a substrate of an electrically insulating material supporting an electrode layer of an electrically conductive material, said substrate and electrode layer having a plurality of layers disposed thereon, the outermost layer being an enzyme layer comprising at least one enzyme, preferable an enzyme layer comprising a polymer matrix and at least one enzyme embedded in said polymer matrix;

b. providing an aqueous dispersion or colloid solution of (i) a water-resistant polymer and (ii) a protein; and c. dispensing said dispersion or colloid solution on said enzyme layer and allowing said dispersion/colloid solution to dry thereby forming an outer layer.

The outer layer is typically deposited as a cover layer onto the enzyme layer. In this case, after solvent evaporation of the dispersion a stable cover layer is formed; typically directly on the enzyme layer. By a direct coating of the outer layer onto the enzyme layer, the outer layer is attached to the underlying enzyme layer by physical adhesion without the need for a mechanical fixation, or the use of glue or an adhesive layer.

When the outer layer is used as outermost cover layer (which is preferred), it is directly in contact with the test sample and alone regulates the diffusion of the analytes necessary for the sensing reaction.

In some important embodiments, the protein is an enzyme, in particular selected from creatinase and other hydrolases, most preferably from creatinase.

The method will provide an enzyme sensor as describe hereinabove and with the features specified under the heading "Enzyme sensors".

Step a

The first step of providing a substrate of an electrically insulating material supporting an electrode layer of an electrically conductive material, wherein the substrate and electrode layer have a plurality of layers disposed thereon, and wherein the outermost layer is an enzyme layer comprising at least one enzyme, preferable an enzyme layer comprising a polymer matrix and at least one enzyme embedded in said polymer matrix, can be achieved by conventional means. One example hereof is described in Example 1.

Step b

In step b., an aqueous dispersion or colloid solution of (i) a water-resistant polymer and (ii) a protein is provided. In some embodiments, the aqueous dispersion or colloid solution may further comprise (iii) polymer particles.

The nature of the water-resistant polymer, the protein and the polymer particles is described further above under the heading "The outer layer". Also, the relative amount of these constituents are described under the same heading taking into account that any solvents are not included in the amounts indicated above for the dried outer layer.

The aqueous dispersion or colloid solution is typically prepared by mixing (i) the water-resistant polymer (typically provided commercially as an aqueous dispersion) with (iii) the polymer particles (also typically provided commercially as an aqueous dispersion) and the (ii) enzyme (typically provided commercially in an aqueous buffer solution). In addition, water (e.g. deionized) is added to provide a suitable viscosity of the dispersion for the purpose of dispensing the dispersion. Typically, the aqueous dispersion/colloid solution has a solids content of 15-25% (w/w).

To prevent the aqueous polymer dispersion/colloid solution from aggregating and to ensure that the dispensing process works satisfactory, it is generally desirable to include one or more low molecular weight additive(s). This is typically low molecular weight non-ionic surfactants e.g. ethoxylated hydrocarbons like Triton X-100, Tergitol TMN3, TMN6 or TMN10.

Step c

In step c., the dispersion or colloid solution is dispersed on the enzyme layer and the dispersion/colloid solution is allowed to dry thereby forming an outer layer.

The film formation and morphology obtained in outer layers casted from aqueous polymer dispersions is very different from the membrane morphology obtained from casted solvent based solutions. In a solvent based polymer solution the different types of macromolecules are intimately blended and randomly distributed throughout the solution. Upon solvent evaporation, the polymer chains approach each other and finally form a film with a high degree of polymer-polymer-interpenetration. In contrast hereto, separated pure water-resistant polymer (like e.g. Eudragit) and protein (like the creatinase enzyme) domains of a certain size, exists at the beginning of the film formation process, when aqueous polymer dispersions are used. Due to the restricted mobility of macromolecules within the colloidal particles, the polymer chains cannot completely interdiffuse. Only in regions close to the particles' surfaces, more or less intimate polymer-polymer blending can be expected. Thus upon water evaporation polymeric films with pure water-resistant polymer and pure protein (e.g. enzyme) domains are formed and the resulting porosity is defined by the distribution of the protein (e.g. enzyme) particles in the polymer dispersion. The polymer-polymer interpenetration only takes place where particles of the water-resistant polymer have intimate contact and it is much lower than in the case of films prepared from organic solutions. In order for the protein phase (e.g. enzyme phase) to be interconnecting from one side of the outer layer to the other, for securing permeability of the outer layer, the protein content most preferably should be above the percolation threshold, which theoretically is around approximately 15% v/v of the outer layer. After water uptake and leaching of the protein pores of the sizes 5-15 nm are filled with water and the diffusion of the analyte and $H_2O_2$ happens through these.

The outer layer is prepared from the aqueous dispersion/colloid solution prepared in step b.

In some interesting embodiments, the aqueous dispersion/colloid solution further comprises polymer particles. Because the water-resistant polymer and the pore-forming polymer particles are physically incompatible, a co-continuous two-phase membrane morphology is formed upon drying of the dispersion/colloid solution. The pore-forming polymer particles are homogeneously distributed throughout the polymer phase and thereby provide connectivity throughout the polymer binder phase.

The porosity of the outer layer and thus the permeability can be provided by the pore-forming hard polymer particles in addition to the porosity provided by the protein(s). Thus, from the permeability point of view there is no limitation when electing the polymer particles. The polymer material used for the hard polymer particles can generally be any polymer dispersion material or a mixture of polymer materials. Preferably, however, non-toxic or easily applicable materials are used.

The outer layer is prepared from an aqueous colloid solution or dispersion, which is more enzyme friendly than a solvent based outer layer, which is normally used for planar metabolite sensors, thus a creatinine sensor surpassing issue with deactivation of the enzyme during dispensing of the outer layer.

The thickness of the outer layer can be chosen flexibly with regard to the desired use and/or permeation rate. Suitable thicknesses are within the range of 0.5 to 1000 μm, typically in the range of 3 to 500 μm, and more typically in the range of 5 to 50 μm.

The permeation of the outer layer can thus be easily adjusted by varying the coating thickness and/or concentration of the (pore-former) proteins.

Since the permeability of the outer layer can be adjusted as desired, the outer layer provides a fast regeneration of the sensor. In the case of a sensing reaction based for example on the consumption of oxygen, the oxygen permeation and content can be adjusted in such a manner that the sensor regeneration, e.g., the regeneration of the oxygen reservoir, is very fast. Thus, the sensors are particularly useful for multiple-use enzyme sensors.

The method allows the application of the outer layer without damaging lower layers, e.g., the enzyme layer.

The outer layer can for example be applied directly onto the enzyme layer without influencing or otherwise damaging the enzyme(s) of the enzyme layer.

The dispersion/colloid solution is typically dried after the dispensing on the enzyme layer. Essentially, every drying method known in the technical field, in particular those operating at around room temperature, can be used.

Use of the Enzyme Sensor

The enzyme sensor described herein which may be prepared according to the method describe herein can replace any conventional enzyme sensor in a conventional apparatus (e.g. a blood gas analyser). Hence, the enzyme sensors defined herein are primarily characterized by the features of the outer microporous layer and can readily be implemented in existing sensor arrays and cartridges.

Therefore, the use of the enzyme sensor according to the invention can readily be accomplished by the skilled person with reference to conventional methods.

This being said, it is envisaged that the features of the outer layer will also provide advantages to any type of enzyme sensor, including those enzyme sensor concepts for which conventional standards have not yet been established.

General Remarks

Although the present description and claims occasionally refer to a polymer, a sensor, an enzyme, etc., it should be understood that the products and methods defined herein may comprise one, two or more types of the individual constituents or elements. In the embodiments wherein two or more different constituents are present, the total amount of the respective constituents should correspond to the amount defined herein for the individual constituent.

The "(s)" in the expressions: polymer(s), sensor(s), enzyme(s), etc. indicates that one, two or more types of the individual constituents or elements may be present. On the other hand, when the expression "one" is used, only one (1) of the respective constituent or element is present.

Throughout the specification the word "comprise", or variations such as "comprising" or "comprises", will be understood to imply the inclusion of a stated element, integer or step, or groups of elements, integers or steps, but not the exclusion of any other element, integer or step, or groups of elements, integers or steps.

EXAMPLES

Materials

Creatinase enzyme (app. 30 w/w %) in Phosphate buffer, BBI
Deionized water
Eudragit NM30D: a 30 w/w % aqueous dispersion of poly(ethylacrylate-co-methyl-methacrylate) 2:1
PTFE: a 60 w/w % polytetrafluoroethylene dispersion in water, Aldrich 66580
Kollicoat SR30D: a 30 w/w % aqueous dispersion (about 27% polyvinyl acetate, 2.7% povidone and 0.3% sodium lauryl sulfate), BASF Example 1 —Construction of a Creatinine Dual Sensor System In one embodiment the planar enzyme sensor is a thick-film sensor, suitable for the measurement of creatinine in samples of physiological fluids. The thick-film sensor is composed of a dual sensor system comprising a creatine sensor and a creatinine sensor each built up as illustrated in FIG. 1.

Figure 1:
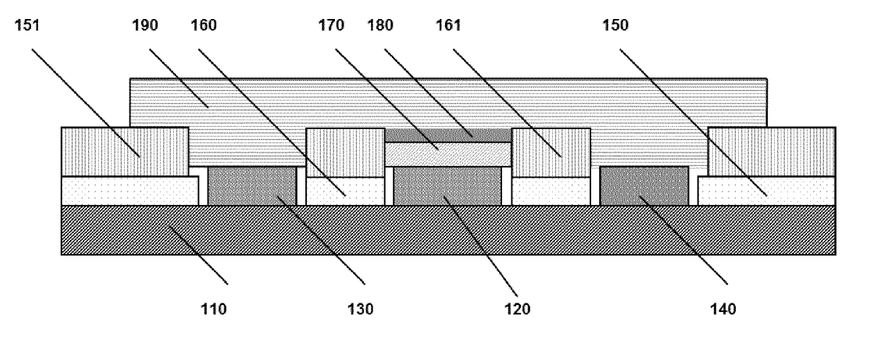
FIG. 1 illustrates the construction of a planar enzyme sensor with reference to the detailed description in Example 1.

Referring to FIG. 1, an electrically insulating alumina substrate 110 of a thickness of 200 µm is provided at one surface with a circular platinum working electrode 120 of a diameter 1000 µm and a thickness of 10 µm, an annular platinum counter electrode 130 of an outer diameter 3000 µm, an inner diameter 2000 µm and a thickness of 10 µm, covering the angular range 30-330° of the outer periphery of the working electrode, and a circular silver/silver chloride reference electrode 140 of a diameter 50 µm, positioned at the outer periphery of the working electrode at 0° . Each of the three electrode structures are connected to the sensor electronics (not shown) across the alumina substrate 110 via platinum filed through holes (not shown) traversing the substrate. Upon operation, the working electrode 120 is polarised to +675 mV vs. the reference electrode 140.

Further on the alumina substrate 110 are two-layered structures of glass and polymer encapsulant. These two-layered structures include an annular structure 160, 161 of an outer diameter 1800 µm, an inner diameter 1200 µm and a thickness of 50 µm surrounding the working electrode 120 and a structure 150, 151 of a thickness 50 µm surrounding the complete electrode system. Both of these two-layered structures consist of an inner layer 150, 160 facing the alumina substrate 110 of ESL glass 4904 from ESL Europe of the United Kingdom of a thickness of 20 µm, and an outer layer 151, 161 of polymer encapsulant from SenDx Medical Inc. of California, USA as disclosed in international patent application WO 97/43634 to SenDx Medical Inc. of California, USA which comprises 28.1% by weight of polyethylmethacrylate (Elvacite, part number 2041, from DuPont), 36.4% by weight of carbitol acetate, 34.3% by weight of silanised kaolin (part number HF900 from Engelhard), 0.2% by weight of fumed silica and 1.0% by weight of trimethoxysilane.

A circular inner layer 170 of cellulose acetate and cellulose acetate butyrate of a diameter 1200 µm and a thickness of 10 µm covers the working electrode 120.

For the creatinine sensor, a circular enzyme layer 180 of creatininase, glutaric aldehyde-treated creatinase and sarcosine oxidase, having a diameter 1200 µm and a thickness of 12 µm, covers the inner layer 170.

For the creatine sensor, a circular enzyme layer 180 of glutaric aldehyde-treated creatinase and sarcosine oxidase, having a diameter 1200 µm and a thickness of 12 µm, covers the inner layer 170.

The outer layer of the invention 190 (cf. Example 2) covers the structure, including the enzyme layer 180, the counter electrode 130 and the reference electrode 140.

Example 2—Testing of Outer Layer Materials

For the purpose of examining various candidates for a suitable outer layer, three different outer layer materials (A, B and C) were produced by mixing the following components:
A: 400 µL Creatinase enzyme dispersion in Phosphate buffer, 2150 µL deionized water, 1020 µL Eudragit NM30D, 1200 µL PTFE dispersion
B: 2000 µL deionized water, 1000 µL Kollicoat SR30D, 2000 µL PTFE dispersion
C: 2350 µL deionized water, 1110 µL Eudragit NM, 1310 µL PTFE dispersion The different outer layer materials were applied on the construction (as 190 in FIG. 1) as described in the example above.

The sensors were tested in reconfigured Radiometer ABL90 flex analyzers, using calibration solutions containing known concentrations of creatine and creatinine. Data were collected and analysed.

The following test was designed to address the availability of the enzyme layer, and thereby the homogeneity of the outer layer. This test compares the sensors response in a solution with and without creatinase inhibitor. The more alike the readout of the two solutions, the more available is the enzyme, and the more suitable is the outer layer. Bicarbonate was used as an inhibitor as it is a relevant and endogenous component in blood.

The results are summarized in Table 1 below, wherein B and C are reference layers.

TABLE 1

| Outer layer material | Sensitivity in solution with 24 mM bicarbonate [pA/µM Creatine] | Sensitivity in solution without bicarbonate [pA/µM Creatine] | Ratio between sensitivities |
|---|---|---|---|
| A | 10.0 | 11.6 | 0.86 |
| B | 6.1 | 8.2 | 0.74 |
| C | 0.08 | 0.15 | 0.53 |

The sensor with outer layer material B shows a lower sensitivity than the sensor with outer layer material A and also a lower ratio between sensitivity. This shows that a smaller part of the enzyme is active and/or available and that sensor B is more exposed to variations in bicarbonate in blood samples.

The sensor with outer layer material C has a very low sensitivity correlating with the absence of the pore forming creatinase enzyme.

In another test round, two outer layer materials (D and E) with the following components was compared:
D: 400 µL Creatinase enzyme dispersion in Phosphate buffer, 3350 µL deionized water, 1020 µL Eudragit NM30D
E: 400 µL Creatinase enzyme dispersion in Phosphate buffer, 2150 µL deionized water, 1020 µL Eudragit NM30D, 1200 µL PTFE dispersion The results are summarized in Table 2 below.

TABLE 2

| Outer layer material | Sensitivity in solution with 24 mM bicarbonate [pA/µM Creatine] | Sensitivity in solution without bicarbonate [pA/µM Creatine] | Ratio between sensitivities |
|---|---|---|---|
| D | 9.9 | 13.7 | 0.73 |
| E | 12.0 | 15.4 | 0.78 |

Even though the sensitivity is higher for sensors with PTFE in the outer layer E compared to the outer layer D with no PTFE, the ability to measure constantly in the presence of inhibitors is better for outer layer E. Thus apart from giving a higher stability towards samples with low $O_2$ concentration, the PTFE particles probably also facilitates the preparation of a more homogenous outer layer.

Relative amounts of constituents in the different outer layer materials (dry basis):

| v/v% | Enzyme | PTFE | Eudragit | Kollicoat |
|---|---|---|---|---|
| A | 11% | 55% | 35% | — |
| B | — | 57% | — | 43% |

-continued

| v/v% | Enzyme | PTFE | Eudragit | Kollicoat |
|---|---|---|---|---|
| C | — | 61% | 39% | — |
| D | 23% | — | 77% | — |
| E | 11% | 55% | 35% | — |

The invention claimed is:

1. A planar enzyme sensor for measuring the concentration of an analyte in a solution, the sensor comprising a substrate of an electrically insulating material supporting an electrode layer of an electrically conductive material, said substrate and electrode layer having a plurality of layers disposed thereon, said plurality of layers at least including:
   a. an enzyme layer comprising at least one first enzyme; and
   b. a microporous outer layer covering the enzyme layer, said outer layer comprising (i) a continuous phase of a water-resistant polymer and (ii) a protein embedded in said continuous phase,
wherein the water-resistant polymer forming said continuous phase of said outer layer is selected from the group consisting of polyvinylacetate and copolymers of ethylacrylate and methylmethacrylate, and
wherein the microporous outer layer further comprises polymer particles embedded in said continuous phase.

2. The sensor according to claim 1, wherein the protein embedded in said continuous phase is a second enzyme.

3. The sensor according to claim 2, wherein the second enzyme embedded in said continuous phase is a hydrolase.

4. The sensor according to claim 2, wherein the second enzyme and the at least one first enzyme are the same enzyme or are different enzymes.

5. The sensor according to claim 1, wherein the polymer particles are polytetrafluoroethylene (PTFE) particles.

6. The sensor according to claim 1, wherein the enzyme layer comprises sarcosine oxidase and creatinase, and wherein the protein in the outer layer is creatinase.

7. The sensor according to claim 1, wherein the enzyme layer comprises a polymer matrix in which said at least one first enzyme is embedded.

8. The sensor according to claim 1, wherein the water-resistant polymer comprises a copolymer of ethylacrylate and methylmethacrylate in an amount of 20-30% based on the total volume of the outer layer.

9. The sensor according to claim 8, wherein the water-resistant polymer comprises at least a second enzyme present in an amount of 10-20% based on the total volume of the outer layer and the polymer particles present in an amount of 50-60% based on the total volume of the outer layer.

10. The sensor according to claim 1, wherein the water-resistant polymer comprises polyvinylacetate in an amount of 20-30% based on the total volume of the outer layer.

11. The sensor according to claim 10, wherein the water-resistant polymer comprises at least a second enzyme present in an amount of 10-20% based on the total volume of the outer layer and the polymer particles present in an amount of 50-60% based on the total volume of the outer layer.

12. The sensor according to claim 1, wherein the water-resistant polymer comprises at least a second enzyme present in an amount of 10-20% based on the total volume of the outer layer and the polymer particles present in an amount of 50-60% based on the total volume of the outer layer.

13. A method for the preparation of the enzyme sensor according to claim 1, said method comprising the steps of:
   a. providing a substrate of an electrically insulating material supporting an electrode layer of an electrically conductive material, said substrate and electrode layer having a plurality of layer disposed thereon, the outermost layer being an enzyme layer;
   b. providing an aqueous dispersion or colloid solution of (i) a water-resistant polymer and (ii) a protein; and
   c. dispensing said dispersion or colloid solution on said enzyme layer and allowing said dispersion or colloid solution to dry thereby forming an outer layer,
wherein the dispersion or colloid solution in step (b) further comprises (iii) polymer particles.

* * * * *

UNITED STATES PATENT AND TRADEMARK OFFICE
CERTIFICATE OF CORRECTION

PATENT NO. : 11,629,368 B2
APPLICATION NO. : 15/776252
DATED : April 18, 2023
INVENTOR(S) : Thomas Kjaer, Thomas Steen Hansen and Lydia Dahl Clausen It is certified that error appears in the above-identified patent and that said Letters Patent is hereby corrected as shown below:

In the Claims

Claim 13, Column 18, Line 30, "layer" should read as --layers--.

Signed and Sealed this
Twenty-fifth Day of July, 2023

Katherine Kelly Vidal
*Director of the United States Patent and Trademark Office*